US011969225B2

(12) United States Patent
Kadokura

(10) Patent No.: US 11,969,225 B2
(45) Date of Patent: Apr. 30, 2024

(54) END EFFECTOR FORCE FEEDBACK TO MASTER CONTROLLER

(71) Applicant: Intuitive Surgical Operations, Inc., Sunnyvale, CA (US)

(72) Inventor: Grant M. Kadokura, San Diego, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 18/135,682

(22) Filed: Apr. 17, 2023

(65) Prior Publication Data
US 2023/0285100 A1    Sep. 14, 2023

Related U.S. Application Data

(63) Continuation of application No. 16/753,298, filed as application No. PCT/US2018/053998 on Oct. 2, 2018, now Pat. No. 11,666,402.
(Continued)

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/35* (2016.02); *A61B 17/00234* (2013.01);
(Continued)

(58) Field of Classification Search
CPC ... A61B 34/37; A61B 34/35; A61B 17/00234; A61B 34/71; A61B 34/76;
(Continued)

(56) References Cited

U.S. PATENT DOCUMENTS 4,160,508 A * 7/1979 Frosch ................... B25J 17/025
414/4
4,604,016 A    8/1986 Joyce
(Continued)

FOREIGN PATENT DOCUMENTS

CN    203092570 U    7/2013
EP    2023844 A2    2/2009
(Continued)

OTHER PUBLICATIONS

Extended European Search Report for Application No. EP18865163.2 dated Jun. 11, 2021, 10 pages.
International Preliminary Report on Patentability for Application No. PCT/US2018/053998, dated Apr. 16, 2020, 14 pages.
International Search Report and Written Opinion for Application No. PCT/US2018/053998, dated Mar. 14, 2019, 20 pages.
(Continued)

*Primary Examiner* — Jaime Figueroa

(57) ABSTRACT

A teleoperated surgical system is provided that includes a surgical instrument that includes an end effector mounted for rotation about a slave pivot axis; a master control input includes a mount member, first and second master grip rotatably secured at the mount member for rotation about a master pivot axis; sensor to produce a sensor signal indicative of a slave grip counter-force about the slave pivot axis; one or more motors to impart a shear force to the mount member, perpendicular to the master pivot axis; one or more processors to convert the sensor signal to motor control signals to cause the motors to impart the feedback shear force to the first and second master grip members.

20 Claims, 9 Drawing Sheets

Related U.S. Application Data

(60) Provisional application No. 62/567,005, filed on Oct. 2, 2017.

(51) Int. Cl.
*A61B 34/35* (2016.01)
*A61B 17/00* (2006.01)
*A61B 17/29* (2006.01)
*A61B 34/30* (2016.01)

(52) U.S. Cl.
CPC .............. *A61B 2017/00398* (2013.01); *A61B 2017/00477* (2013.01); *A61B 2017/2927* (2013.01); *A61B 2034/305* (2016.02); *A61B 34/71* (2016.02); *A61B 34/76* (2016.02)

(58) Field of Classification Search
CPC ........... A61B 2017/00398; A61B 2017/00477; A61B 2017/2927; A61B 2034/305; A61B 17/282; A61B 90/06; A61B 17/29; A61B 2090/065
See application file for complete search history.

(56) References Cited

U.S. PATENT DOCUMENTS

| | | | |
|---|---|---|---|
| 5,116,180 A * | 5/1992 | Fung | B25J 9/1689 414/909 |
| 5,696,837 A | 12/1997 | Green | |
| 5,710,870 A | 1/1998 | Ohm et al. | |
| 5,767,648 A * | 6/1998 | Morel | B25J 9/1628 318/568.1 |
| 5,784,542 A | 7/1998 | Ohm et al. | |
| 6,024,576 A | 2/2000 | Bevirt et al. | |
| 6,102,850 A | 8/2000 | Wang et al. | |
| 6,184,868 B1 | 2/2001 | Shahoian et al. | |
| 6,197,017 B1 | 3/2001 | Brock et al. | |
| 6,377,011 B1 | 4/2002 | Ben-Ur | |
| 6,385,509 B2 | 5/2002 | Das et al. | |
| 6,424,885 B1 * | 7/2002 | Niemeyer | A61B 34/77 600/109 |
| 6,459,926 B1 | 10/2002 | Nowlin et al. | |
| 6,587,750 B2 | 7/2003 | Gerbi et al. | |
| 6,594,552 B1 | 7/2003 | Nowlin et al. | |
| 6,671,581 B2 * | 12/2003 | Niemeyer | A61B 34/37 600/109 |
| 6,714,839 B2 | 3/2004 | Salisbury, Jr. et al. | |
| 6,723,106 B1 | 4/2004 | Charles et al. | |
| 6,817,974 B2 | 11/2004 | Cooper et al. | |
| 6,994,703 B2 | 2/2006 | Wang et al. | |
| 7,155,315 B2 * | 12/2006 | Niemeyer | A61B 34/70 382/128 |
| 7,248,944 B2 | 7/2007 | Green | |
| 7,373,219 B2 | 5/2008 | Nowlin et al. | |
| 7,783,383 B2 | 8/2010 | Eliuk et al. | |
| 7,843,158 B2 | 11/2010 | Prisco | |
| 7,930,066 B2 | 4/2011 | Eliuk et al. | |
| 8,002,767 B2 | 8/2011 | Sanchez et al. | |
| 8,005,571 B2 * | 8/2011 | Sutherland | A61B 34/37 318/568.22 |
| 8,041,459 B2 * | 10/2011 | Sutherland | A61B 90/25 600/407 |
| 8,073,335 B2 | 12/2011 | Labonville et al. | |
| 8,120,301 B2 | 2/2012 | Goldberg et al. | |
| 8,170,717 B2 * | 5/2012 | Sutherland | A61B 34/35 901/14 |
| 8,224,484 B2 * | 7/2012 | Swarup | A61B 34/74 700/245 |
| 8,271,130 B2 | 9/2012 | Hourtash et al. | |
| 8,316,961 B2 | 11/2012 | Isobe et al. | |
| 8,343,171 B2 | 1/2013 | Farritor et al. | |
| 8,396,598 B2 * | 3/2013 | Sutherland | A61B 34/71 901/14 |
| 8,423,186 B2 | 4/2013 | Itkowitz et al. | |
| 8,444,631 B2 | 5/2013 | Yeung et al. | |
| 8,479,969 B2 | 7/2013 | Shelton, IV | |
| 8,620,473 B2 | 12/2013 | Diolaiti et al. | |
| 8,644,988 B2 | 2/2014 | Prisco et al. | |
| 8,992,565 B2 | 3/2015 | Brisson et al. | |
| 9,002,518 B2 * | 4/2015 | Manzo | A61B 90/98 901/19 |
| 9,014,856 B2 * | 4/2015 | Manzo | A61B 34/37 901/19 |
| 9,043,019 B2 | 5/2015 | Eliuk et al. | |
| 9,050,120 B2 * | 6/2015 | Swarup | A61B 34/71 |
| 9,220,567 B2 * | 12/2015 | Sutherland | A61B 34/70 |
| 9,244,523 B2 | 1/2016 | Ogawa et al. | |
| 9,244,524 B2 | 1/2016 | Inoue et al. | |
| 9,339,343 B2 * | 5/2016 | Swarup | A61B 34/71 |
| 9,423,869 B2 | 8/2016 | Yanagihara | |
| 9,632,577 B2 | 4/2017 | Ogawa et al. | |
| 9,649,174 B2 * | 5/2017 | Swarup | A61B 34/71 |
| 9,671,860 B2 | 6/2017 | Ogawa et al. | |
| 9,913,694 B2 | 3/2018 | Brisson | |
| 2001/0018591 A1 | 8/2001 | Brock et al. | |
| 2003/0004610 A1 * | 1/2003 | Niemeyer | A61B 34/70 700/245 |
| 2003/0060927 A1 * | 3/2003 | Gerbi | A61B 34/71 606/130 |
| 2003/0195664 A1 | 10/2003 | Nowlin et al. | |
| 2004/0039485 A1 * | 2/2004 | Niemeyer | A61B 34/77 700/245 |
| 2006/0106493 A1 * | 5/2006 | Niemeyer | A61B 34/30 700/245 |
| 2007/0005002 A1 | 1/2007 | Millman et al. | |
| 2007/0142968 A1 | 6/2007 | Prisco et al. | |
| 2007/0151390 A1 | 7/2007 | Blumenkranz et al. | |
| 2007/0151391 A1 | 7/2007 | Larkin et al. | |
| 2007/0239028 A1 | 10/2007 | Houser et al. | |
| 2008/0046122 A1 * | 2/2008 | Manzo | A61B 90/98 700/245 |
| 2009/0062813 A1 | 3/2009 | Prisco et al. | |
| 2009/0088774 A1 * | 4/2009 | Swarup | A61B 34/37 901/31 |
| 2009/0088775 A1 * | 4/2009 | Swarup | A61B 34/71 700/264 |
| 2009/0216374 A1 | 8/2009 | Low et al. | |
| 2010/0073150 A1 | 3/2010 | Olson et al. | |
| 2010/0256558 A1 | 10/2010 | Olson et al. | |
| 2011/0087238 A1 | 4/2011 | Wang et al. | |
| 2011/0106141 A1 | 5/2011 | Nakamura | |
| 2011/0118748 A1 | 5/2011 | Itkowitz | |
| 2011/0290856 A1 | 12/2011 | Shelton, IV et al. | |
| 2012/0116371 A1 | 5/2012 | Houser et al. | |
| 2012/0123441 A1 | 5/2012 | Au et al. | |
| 2012/0179169 A1 * | 7/2012 | Swarup | A61B 34/37 606/130 |
| 2012/0265051 A1 | 10/2012 | Fischer et al. | |
| 2013/0006268 A1 * | 1/2013 | Swarup | A61B 34/74 606/130 |
| 2013/0103050 A1 | 4/2013 | Richmond et al. | |
| 2013/0110130 A1 * | 5/2013 | Manzo | A61B 34/71 606/130 |
| 2013/0172906 A1 * | 7/2013 | Olson | A61B 34/30 606/130 |
| 2013/0289767 A1 | 10/2013 | Lim et al. | |
| 2013/0296737 A1 | 11/2013 | McMillan et al. | |
| 2014/0135793 A1 | 5/2014 | Cooper et al. | |
| 2014/0330073 A1 | 11/2014 | Ko et al. | |
| 2014/0371762 A1 * | 12/2014 | Farritor | B25J 9/1602 901/46 |
| 2015/0130599 A1 * | 5/2015 | Berkley | G08B 6/00 340/407.2 |
| 2015/0360365 A1 | 12/2015 | Fudaba et al. | |
| 2016/0213437 A1 | 7/2016 | Richmond et al. | |
| 2019/0015169 A1 | 1/2019 | Verner et al. | |
| 2019/0142536 A1 * | 5/2019 | Steger | A61B 34/20 606/130 |
| 2019/0201137 A1 | 7/2019 | Shelton, IV et al. | |
| 2020/0237461 A1 | 7/2020 | Kadokura | |

(56) References Cited

U.S. PATENT DOCUMENTS

2020/0278265 A1   9/2020  Suresh
2020/0330172 A1  10/2020  Farritor et al.
2021/0093409 A1   4/2021  Overmyer et al.

FOREIGN PATENT DOCUMENTS

| KR | 20150007020 A | 1/2015 |
|---|---|---|
| WO | WO-2006120666 A1 | 11/2006 |
| WO | WO-2012127404 A2 | 9/2012 |
| WO | WO-2013018934 A1 | 2/2013 |
| WO | WO-2013059643 A1 | 4/2013 |
| WO | WO-2013169303 A1 | 11/2013 |
| WO | WO-2015148293 A1 | 10/2015 |
| WO | WO-2015153642 A1 | 10/2015 |
| WO | WO-2017130562 A1 | 8/2017 |

OTHER PUBLICATIONS

Office Action for CN Application No. 2018800755690, dated Dec. 19, 2022, 38 pages.
Office Action for U.S. Appl. No. 16/753,298 dated Sep. 2, 2022, 22 pages.
Okamura A.M., "Haptic Feedback in Robot-Assisted Minimally Invasive Surgery," Current Opinion in Urology, Jun. 24, 2009, National Institute of Health Public Access, vol. 19 (1), 10 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for EP Application No. 18865163.2, dated Oct. 4, 2023, 05 pages.

\* cited by examiner

END EFFECTOR FORCE FEEDBACK TO MASTER CONTROLLER

RELATED APPLICATIONS

This application is a continuation of U.S. application Ser. No. 16/753,298, filed on Apr. 2, 2020, and published as US 2020/0237461 A1 on Jul. 30, 2020, which is a U.S. National Stage Filing under 35 U.S.C. 371 from International Application No. PCT/US2018/053998, filed on Oct. 2, 2018, and published as WO 2019/070734 A1 on Apr. 11, 2019, which claims the benefit of priority to U.S. Provisional Patent Application Ser. No. 62/567,005, filed on Oct. 2, 2017, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances. In manual minimally invasive surgery, surgeons feel the interaction of the instrument with the patient via a long shaft, which eliminates tactile cues and masks force cues. In teleoperation surgery systems, natural force feedback is largely eliminated because the surgeon no longer manipulates the instrument directly. Kinesthetic or force feedback systems typically measure or estimate the forces applied to the patient by the surgical instrument.

SUMMARY

In one aspect, a teleoperated surgical system is provided that includes a surgical instrument that includes a shaft, an end effector that includes a first cantilever beam, mounted for rotation about a slave pivot axis disposed at the distal end portion of the shaft. A master control input includes a mount member and a first master grip member mounted upon the mount member for a direction of movement along a first path relative to the mount member. A sensor is configured to sense a magnitude of produce a slave cantilever beam force. One or more actuators are configurable to impart a force to the mount member. One or more processors are configured to cause the one or more actuators to impart a feedback force to the mount member, having a magnitude indicative of the magnitude of the slave cantilever beam force and having a direction of movement along a second path separate from the first path.

In another aspect, a method is provided to provide at a master control input an indication of a grip force at a slave end effector portion mounted to a distal end of a surgical instrument shaft in which the master control input includes a mount member and a first master grip member, mounted for a direction of movement along a first path. The method includes producing a sensor signal indicative of magnitude of a grip moment about a slave pivot axis of the end effector and producing a feedback force at the mount member, having a magnitude based upon the sensor signal and having a direction of movement along a second path separate from the first path.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Teleoperated Surgical System

Figure 1:
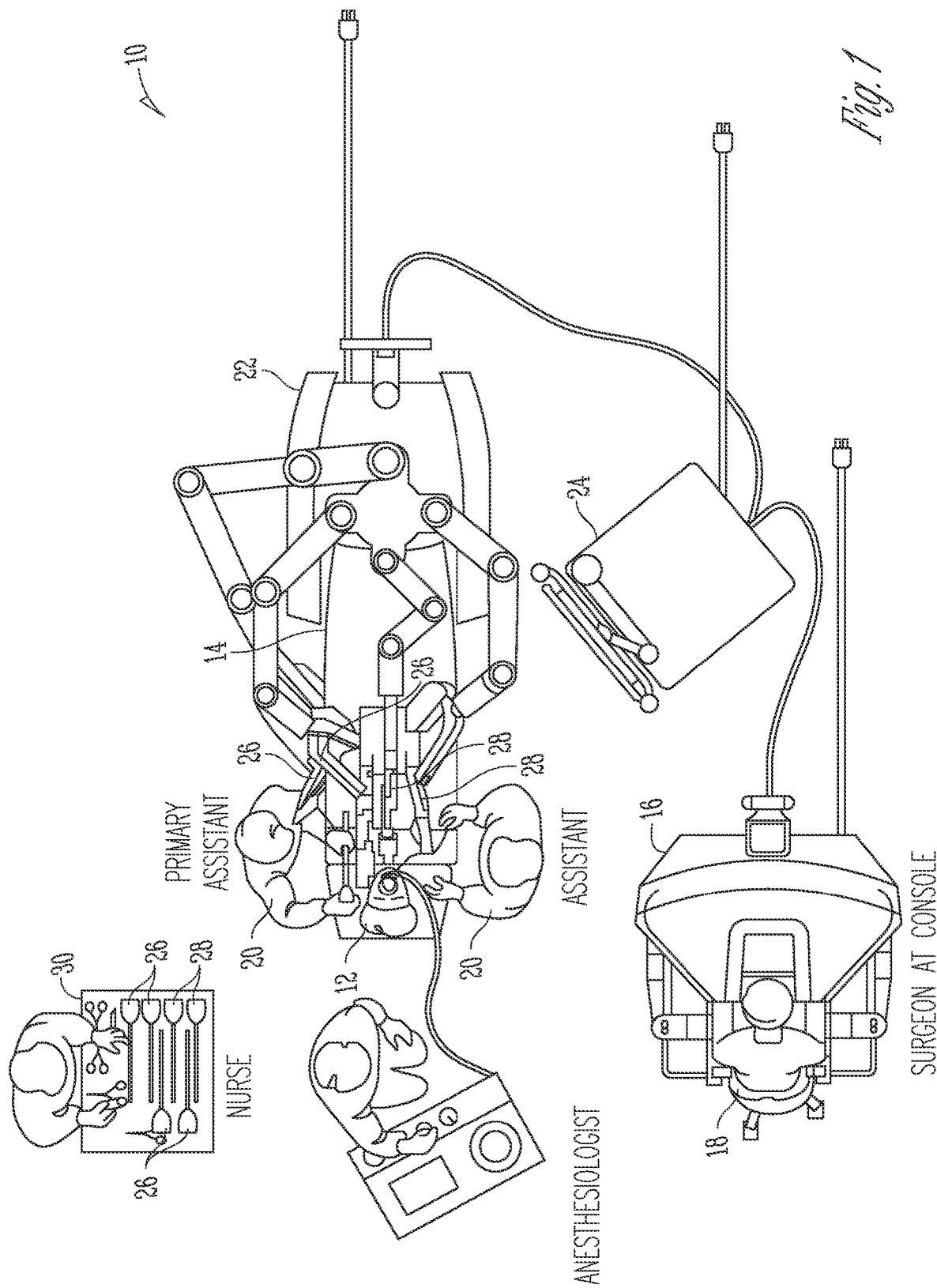
FIG. 1 is an illustrative plan view of a minimally invasive teleoperated surgical system in accordance with some embodiments.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 also may participate in the procedure. The minimally invasive teleoperated surgical system 10 further includes one or more patient-side cart (PSC) 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
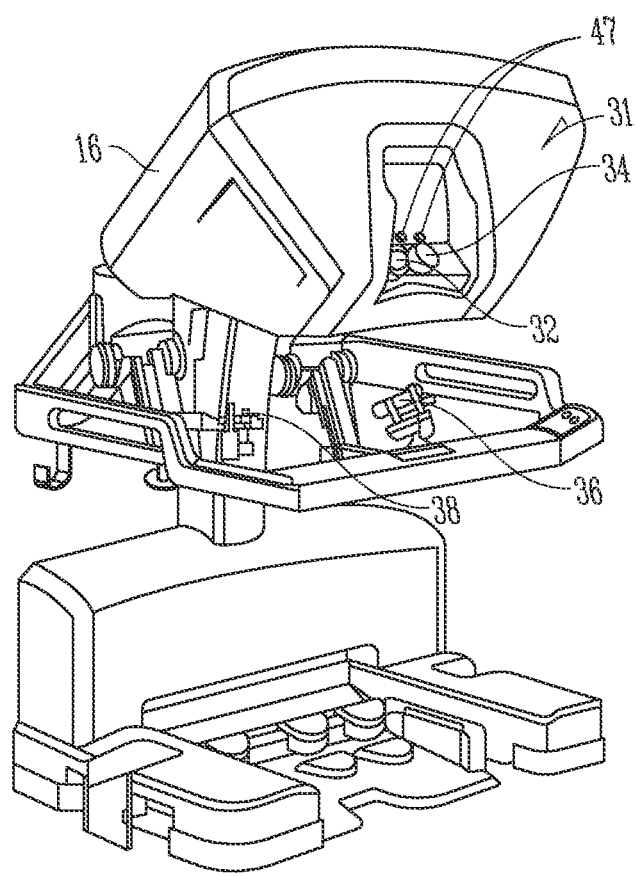
FIG. 2 is a perspective view of the surgeon's console of the system of FIG. 1.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive larger-scale hand control movements. One or more surgical instruments installed for use on the patient-side cart 22 move in smaller-scale distances that correspond to a surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints.

Figure 3:
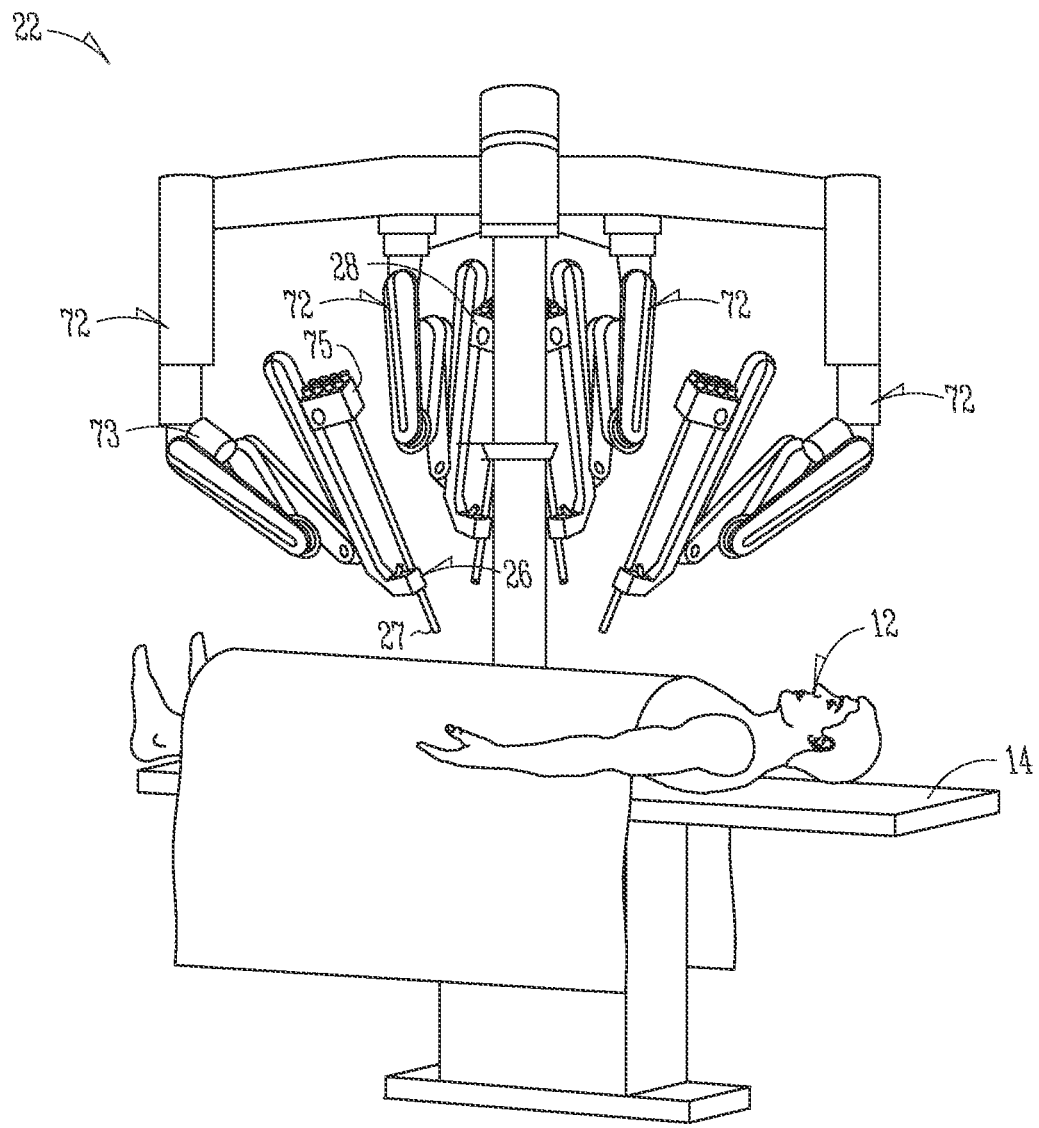
FIG. 3 is a perspective view of a patient-side cart of the system of FIG. 1.

FIG. 3 is a perspective view of a patient-side cart 22 of a minimally invasive teleoperated surgical system 10, in accordance with some embodiments. The patient-side cart 22 includes four mechanical support arms 72. A surgical instrument manipulator 73, which includes actuators such as motors, to control instrument motion, is mounted at the end of each support arm assembly 72. Additionally, each support arm 72 can optionally include one or more setup joints (e.g., unpowered and/or lockable) that are used to position the attached surgical instrument manipulator 73 in relation to the patient for surgery. While the patient-side cart 22 is shown as including four surgical instrument manipulators 73, more or fewer surgical instrument manipulators 73 may be used. A teleoperated surgical system will generally include a vision system that typically includes an endoscopic camera instrument 28 for capturing video images and one or more video displays for displaying the captured video images.

In one aspect, for example, individual surgical instruments 26 and cannulas 27 are removably coupled to manipulator 73, with the surgical instrument 26 inserted through the cannula 27. One or more teleoperated actuator motors of the manipulator 73 move the surgical instrument 26 as a whole to position it in relation to a patient 12. Each support arm assembly includes an instrument carriage 75. A surgical instrument 26 is detachably connected to an instrument carriage 75. In one aspect, the instrument carriage 75 houses one or more teleoperated actuator motors (not shown) inside that provide a number of controller motions that the surgical instrument 26 translates into a variety of movements of an end effector at a distal end of the surgical instrument 26. Thus, the teleoperated actuator motors within the instrument carriage 75 move individual components of the surgical instrument 26 rather than the instrument as a whole. Inputs to control either the instrument as a whole or the instrument's components are such that the input provided by a surgeon or other medical person to a control input 36 (a "master" command) are translated into a corresponding action by a surgical instrument end effector (a "slave" response). A wire cable-based force transmission mechanism or the like is used to transfer the motions of each of the remotely located teleoperated actuator motors to a corresponding instrument-interfacing actuator output located on instrument carriage 75. In some embodiments, the surgical instrument 26 is mechanically coupled to a first actuator motor, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of jaws of an end effector, for example.

Figure 4:
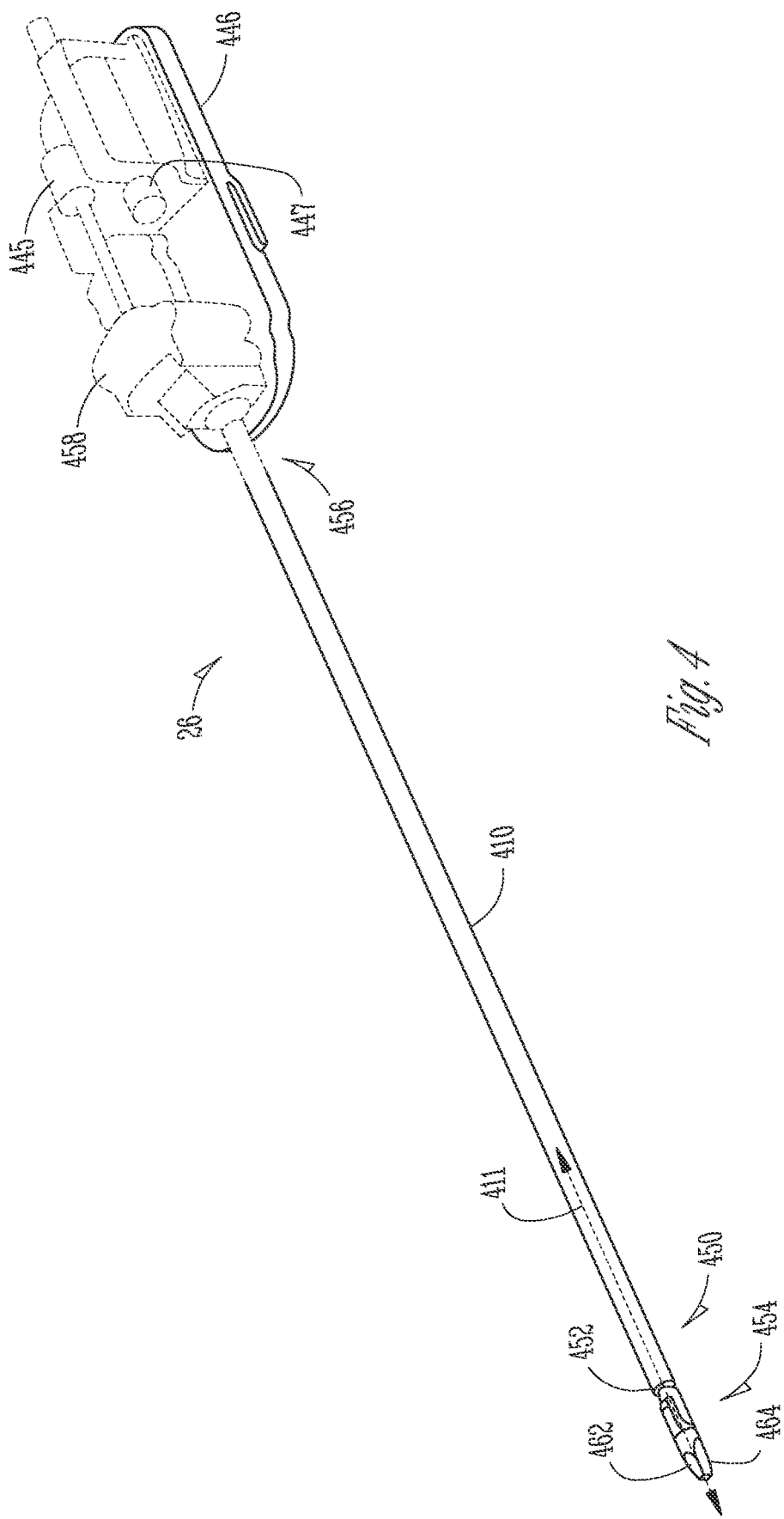
FIG. 4 is a perspective view of a surgical instrument in accordance with some embodiments.

FIG. 4 is a perspective view of a surgical instrument 26 in accordance with some embodiments. The surgical instrument 26 includes an elongated hollow tubular shaft 410 having a centerline longitudinal axis 411. The shaft 410 includes a distal end portion 450 for insertion into a patient's body cavity and proximal end portion 456 that that is mechanically secured to a chassis 440 that mounts motor-driven drive elements 458 that impart forces to cables (not shown) extending within the shaft that are coupled to actuate a surgical end effector 454. A cable drive mechanism 458 may include a motor-driven spindle (not shown), for example. Actuator motors 445, 447 may be mounted on the chassis 440 itself or on the instrument carriage 75, for example. The end effector 454 is coupled to the distal end portion 450 of shaft 410 by a wrist 452. Preferably, wrist 452 provides at least two degrees of freedom. In some embodiments, the wrist 452 is rotatable about the centerline longitudinal axis 411, thereby providing three orientational degrees of freedom for surgical end effector 454 at a surgical site internal to a patient's 12 body cavity. The motor driven drive elements 458 exert forces upon the cables to impart motion to the end effector 454 such as opening or closing of jaws and (x, y) rotational motion of a wrist, for example. A variety of alternative end effectors for alternative tools may be mounted at the distal end portion 450 of the shaft 410 such as forceps, scissors, and clip applier, which include first and second end effector cantilever beams 462, 464 which pivot relative to each other so as to define a pair of end effector jaws, for example. Other end effectors, such as a scalpel and electrocautery probe may have a single end effector element, for example.

Figure 5:
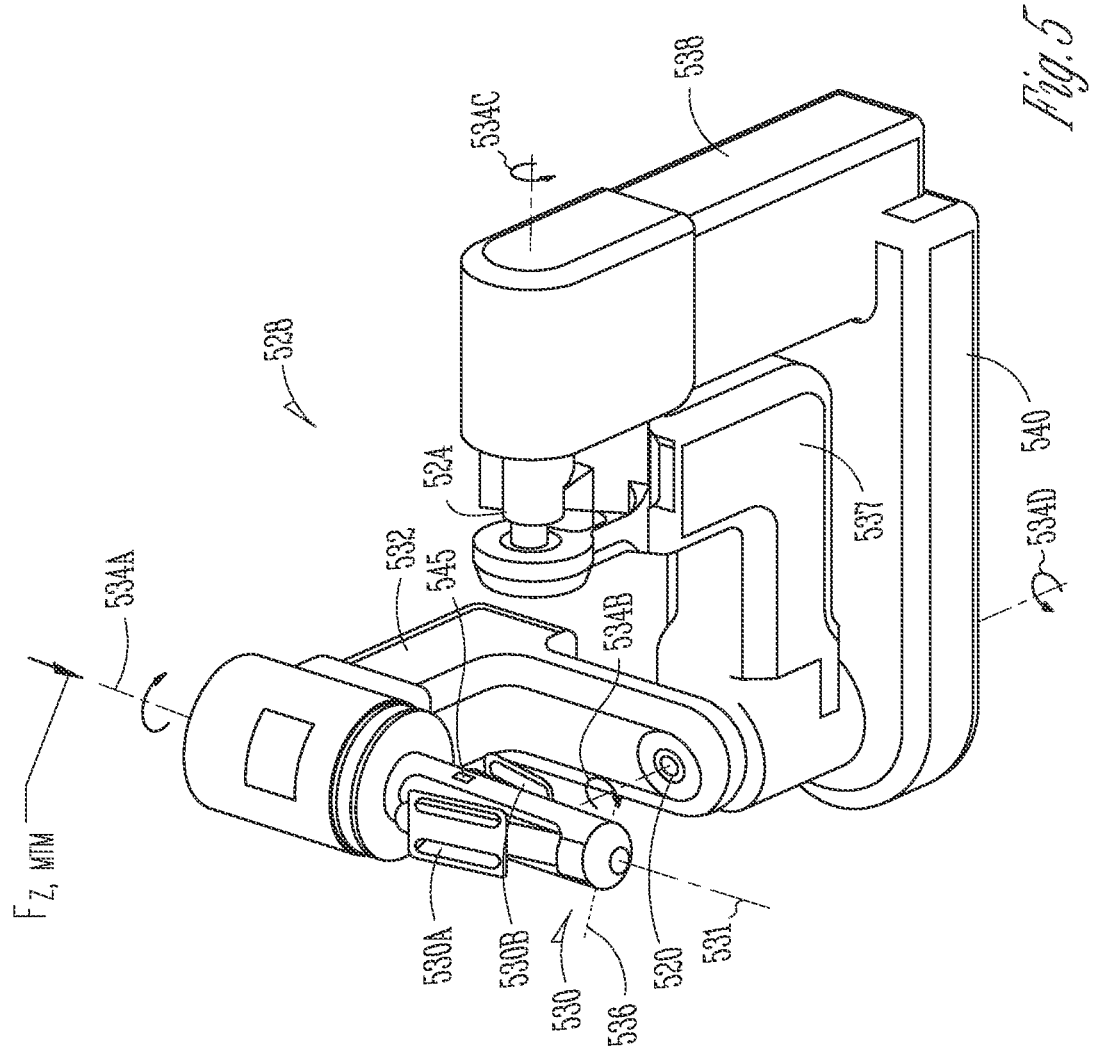
FIG. 5 is an illustrative perspective showing details of a master control input mounted upon a gimbal assembly within the surgeon console 16 of FIG. 2 in accordance with some embodiments.

FIG. 5 is an illustrative perspective showing details of an control input 36 mounted upon a gimbal assembly 528 within the surgeon console 16 of FIG. 2 in accordance with some embodiments. The control input 36, which also is referred to as a master tool manipulator (MTM), includes a mount member configured as a handle 530 and first and second articulable grip members 530a, 530b mounted upon the handle 530. The handle acts as a mount member to mount the first and second grip members 530a, 530b; The first and second grip members 530a, 530b upstand at an incline from opposite sides of the handle 530. The first and second grip members are inclined relative to the handle 530 with their distal ends spaced closer together and their proximal ends spaced farther apart. The first and second grip members have an angle $\alpha$ between their distal ends that may vary according to forces exerted by a surgeon. In some embodiments, the angle $\alpha$ is an acute angle. The first and second grip members 530a, 530b are secured to the handle to articulate relative to the mount member 530. More specifically, in accordance with some embodiments, the first and second grip members 530a, 530b are secured to the handle to pivot about a master pivot axis 536 to follow a first path (not shown). A biasing member (not shown) urges the grip members 530a, 530b apart. A surgeon may grip the grip members 530a, 530b and apply forces to urge them along the first path so as to cause them to move closer together or to cause the biasing member to urge them in an opposite direction along the first path to cause them to move apart. The mount member handle 530 may include a grip actuation sensor (not shown) such as a Hall effect device to sense movement of the grip members along the first path. Finger loops may be attached to the handle to avoid slipping from the grip members. The grip members 530a, 530b are operatively coupled through kinematics, for example, to control motion of a slave end effector 454 at the distal end portion 450 of a surgical instrument shaft 410 in response to motion of the grip members 530a, 530b along the first path. The slave end effector 454 may include first and second cantilever beams 462, 464 that open and close in response to the surgeon's causing corresponding movement of the first and second grip members 530a, 530b closer together and farther apart, for example.

More particular, in some embodiments, a four-degree of freedom gimbal 528 allows rotation of the actuatable mount member handle 530 about three axes, axis 534a, axis 534b, and axis 534c. The handle 530 is coupled to a first elbow-shaped link 514 by a first pivotal joint 16. First link 532 is coupled to a second elbow-shaped link 537 by a pivotal joint 520. Second link 537 is pivotally coupled to a third elbow-shaped link 538 by a pivotal joint 524. In some embodiments, motors of arm 538 and gimbal 528 are capable of actively applying positional and orientational forces to mount member handle 530, thereby providing tactile feedback to the surgeon. In particular, the gimbal motors can be configured through control signals to impart a feedback force $F_{Z,MTM}$ along a second path separate from the first path. In the illustrative embodiment of FIG. 5, the feedback force $F_{Z,MTM}$ is imparted parallel to an axis 531 of the handle 530 in a direction toward the vertex of the angle, which is directed perpendicular to a master pivot axis 536, such that the feedback force is felt equally by a surgeon's fingers on each of the grip members 530a, 530b. The gimbal 528 includes links 532, 537, 538. Gimbal 528 is mounted to platform 540 so as to rotate about axis 534d, and links 532, 537, 538 define additional axes 534a, 534b and 534c. Handle 530 is mounted to gimbal 528 by an actively driven joint for motion about axis 534d. Hence, gimbal 528 provides four driven orientational degrees of freedom, including a redundant orientational degree of freedom. Gimbal 528, arm 538, and the driving motors for these joints are described in more detail in U.S. Pat. No. 6,714,839, entitled "Master Having Redundant Degrees of Freedom", the full disclosure of which is expressly incorporated by this by reference.

The grip members 530a and 530b of mount member handle 530 pivot passively about a master pivot axis 536 with no drive motor provided for feedback from the slave to control their pivot. In the exemplary embodiment, an actuator 545 is mounted to generate a master grip signal indicating the angular separation between grip members 530a and 530b. In some embodiments, the actuator 545 includes a Hall effect transducer in one of the grip members and a magnet mounted in the other, so that handle 530 generates a master grip signal indicating the angular separation between grip members 530a and 530b. A biasing system urges the grip members 530a and 530b apart, and the grip members may include loops of Velcro™ or the like to more firmly position the grip members relative to a thumb and finger of a system operator. A wide variety of grip member structures might be used within the scope of the disclosure, including any surgical instrument handles, optionally including rigid or flexible loops for the thumb and/or fingers, for example. Control relationships between the grip members and slave end effector jaws is explained in more detail in U.S. Pat. No. 6,594,552, entitled, "Grip Strength with Tactile Feedback for Robotic Surgery", the full disclosure of which is expressly incorporated by this by reference.

Figure 6:
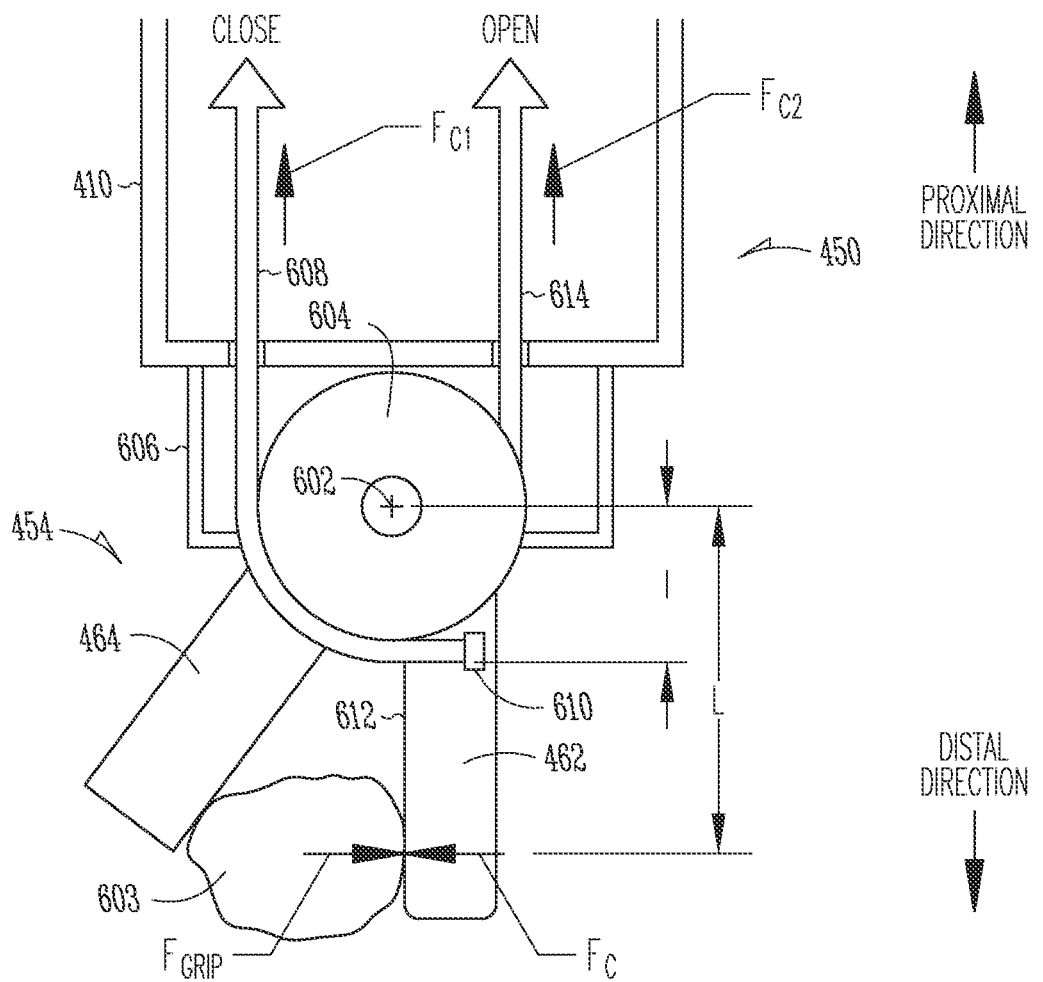
FIG. 6 is an illustrative side cross-section partially transparent view of an end effector of the surgical instrument of FIG. 4 in accordance with some embodiments.

FIG. 6 is an illustrative side cross-section partially transparent view of an end effector 454 of the surgical instrument 26 of FIG. 4 in accordance with some embodiments. The end effector 454 includes a first and second cantilever beams 462, 464 disposed at a distal end 450 of the shaft 410 of the surgical instrument 26. The first cantilever beam 462 is mounted for rotation about a slave pivot axis 602. The end effector 454 is mounted at the distal end portion 450 of the elongated shaft 410. The first and second cantilever beams 462, 464 act as first and second jaws that may be opened to capture anatomical tissue 603 between them and may be closed to grip the anatomical tissue 603 between them. The first cantilever beam 462 may act as a first jaw. The second cantilever beam 464 may act as a second jaw. In some embodiments, the first cantilever beam 462 is rotatable about the slave pivot axis 602 and the second cantilever beam 464 has a fixed position at the distal end of the shaft such that the first cantilever beam 462, acting as a first jaw, moves relative to the fixed second cantilever beam 464, acting as the second jaw. In an alternative embodiment (not shown), both the first and second cantilever beams 462, 464 may be rotatable about the slave pivot axis 602, for example. The first cantilever beam 462 that is integrally secured to a first pulley 604, which is rotatably mounted to a clevis 606 (represented by dashed lines) to rotate in unison about the slave pivot axis 602. A first cable 608 extends longitudinally within the hollow shaft 410. A proximal end (not shown) of the first cable 608 is operatively coupled to an actuator motor to impart a first cable force $F_{C1}$ upon the cable to rotate the first beam 462 toward the second beam 464 to 'close' the jaws. A distal end portion of the first cable wraps about a perimeter groove portion of the first pulley 604. An anchor 610, such as a crimp in the first cable 608, secures a distal end of the first cable 606 to the first cantilever beam so that a first cable force $F_{C1}$ exerted in a proximal direction upon a proximal end of the first cable 608 imparts a force upon the distal end of the first cable that the rotatably mounted first cantilever beam 462 translates to a rotational force $F_{C1}$ exerted at a working/tissue engagement surface 612 of the first cantilever beam 462 in a direction that is normal to the slave pivot axis 602, to urge rotation of the first cantilever beam 462 in a direction toward the second beam 464 to close the jaws.

A distal end portion of a second cable 614 that extends longitudinally within the hollow shaft 410 wraps about a perimeter groove portion of a second pulley (not shown) mounted to the clevis 606 in parallel with the first pulley 604. A proximal end (not shown) of the second cable 614 is operatively coupled to an actuator motor to impart a second cable force $F_{C2}$ upon the second cable 614 to rotate the first beam 462 away the second beam 464 to 'open' the jaws. A distal end of the second cable 614 is secured to the first cantilever beam 462 such that a proximal direction second cable force $F_{C2}$ exerted on the second cable 614 imparts causes the rotatably mounted first cantilever beam 462 to rotate in a direction away from the second beam 464 to open the jaws. In some embodiments the first and second cables 608, 614 include center segments that include elongated tubules and end segments that comprise wire.

During gripping of anatomical tissue 603, for example, a cable drive mechanism 458 described above, causes the first cable 608 to exert the first cable force $F_C$ axially upon the first cable 608 to a impart rotation force to the first cantilever beam 462 that balances a slave grip counter-force $F_{grip}$ imparted to the working surface 612 of the first cantilever beam 462 by the gripped tissue 603. The grip counter-force $F_{grip}$ balances the first beam force first cable force $F_C$. The balanced first cable force $F_C$ and the grip force $F_{grip}$ each produce a grip moment about the slave pivot axis, $M_{grip}$ represented in the following formulation.

$$M_{grip} = F_{grip} \cdot L = F_c \cdot l \qquad (1)$$

where L represents a distance from the point where the slave grip force $F_{grip}$ is applied to the slave pivot axis, and l represents a distance from the first cable anchor 610, where the first cable 608 is secured to the first cantilever beam 462, and the slave pivot axis 602. Thus, during gripping of anatomical tissue 603, the first cable force $F_C$ has a magnitude to counter-balance the slave grip force $F_{grip}$.

Figure 7:
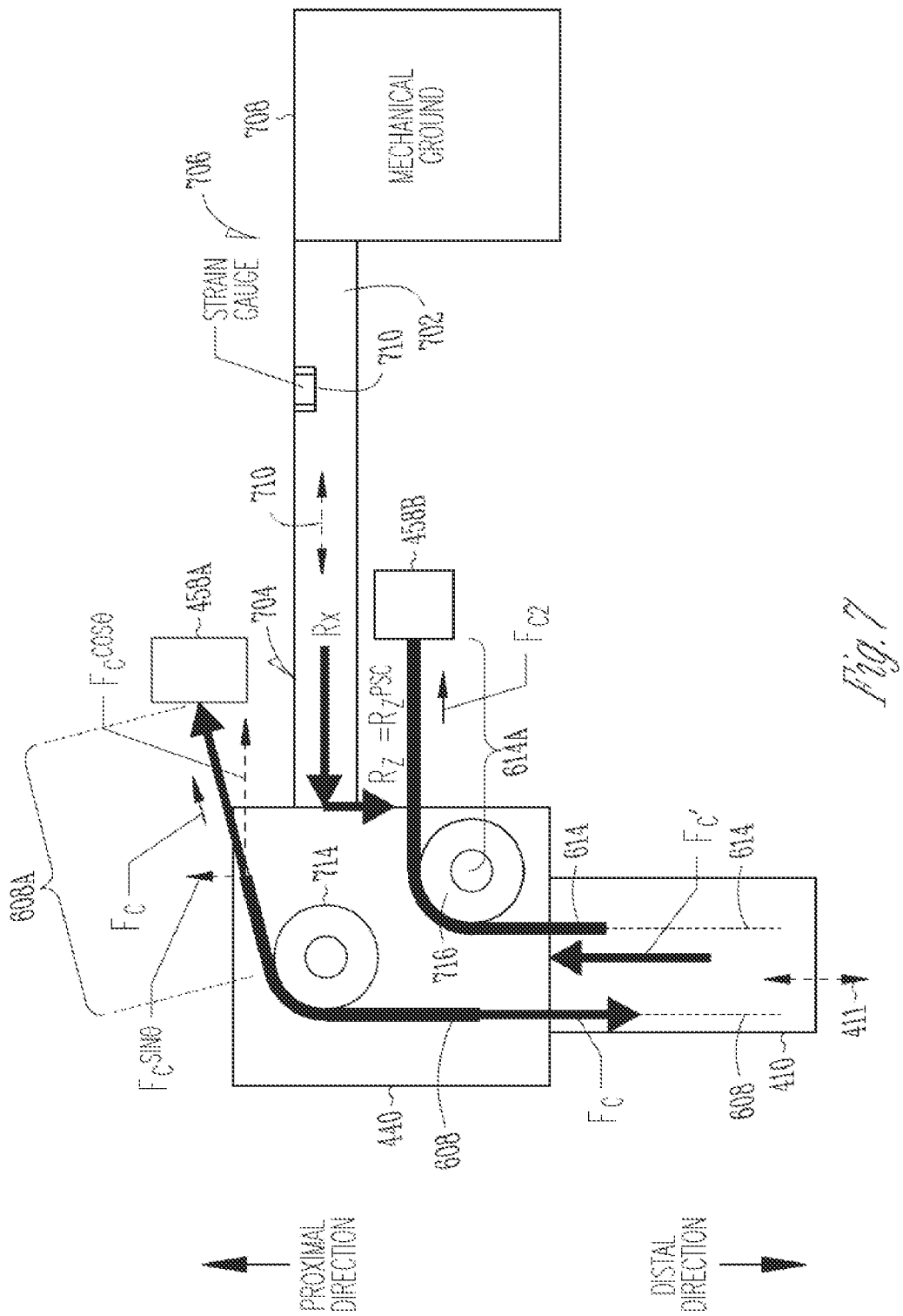
FIG. 7 is an illustrative side view of the chassis of the surgical instrument of FIG. 4 suspended from a support beam in accordance with some embodiments.

FIG. 7 is an illustrative side view of the chassis 440 of the surgical instrument 26 of FIG. 4 suspended from a support beam 702 in accordance with some embodiments. The chassis 440 is secured to the proximal end portion 456 of the shaft 410 of the surgical instrument 26. A first end portion 704 of the support beam 702 is secured to the chassis 440 and a second end portion 706 of the support beam 702 is secured to a mechanical ground 708. The support beam has a longitudinal axis 710 (the beam axis) that extends between its first and second ends 704, 706. In some embodiments, a mechanical support arm 72 acts as the mechanical ground 708. The center axis 411 of the hollow tube 410 is normal to the support beam axis 710.

A strain sensor 712 contacts the support beam 702 and is configured to measure strain imparted to the support beam 702. In some embodiments, the strain sensor includes resistive strain gauge, optical fiber Bragg grating, piezoelectric sensor. Strain is a measure of the amount of deformation of a body, such as the support beam and the strain sensor 702, due to an applied force. More specifically, strain can be defined as the fractional change of length. The mechanical ground 708 acts as a fixed reference structure that does not exhibit strain due to the cable force $F_C$ or a slave grip force $F_{grip}$.

A third pulley 714 is rotatably secured to the chassis 440. A proximal end portion of the first cable 608 wraps about a perimeter groove portion of the third pulley 714. A first cable drive mechanism 458a, which is secured to the mechanical ground 708, is configured to impart the first force $F_C$ upon the first cable 608. In some embodiments, the first cable drive mechanism 458a includes a motor driven rotatable spindle mechanically coupled to a proximal end portion of the first cable 608. The third pulley 714 and the first cable drive mechanism 458a are disposed at a vertical offset from each other relative to the support beam axis 702 such that a proximal segment 608a of the first cable 608 between them extends at an offset angle θ from the support beam axis 710. The first cable drive mechanism 458a may impart a first cable force $F_C$ to the offset angled first cable segment 608a to close the jaws. The first cable force $F_C$ applied to the offset first cable segment 608a results in a first cable offset force component $F_C \sin\theta$ upon the support beam 702 that is parallel to the shaft axis 411 and normal to the support beam axis 710 and a first cable offset force component $F_C \cos\theta$ upon the support beam 702 that is perpendicular to the shaft axis 411 and that is parallel to the beam axis 710. In reaction to the first cable force components, the support beam 702 produces reactive normal and parallel beam forces $R_X$ and $R_Z$. The reactive beam force $R_Z$, which shall be referred to herein as $F_{z,PSC}$, the z-force measured on the system side, acts as a strain force applied at the first end 704 of the support beam 702. The strain force $F_Z$ is imparted in a direction normal to the support beam axis.

It will be appreciated that the first cable force $F_C$ imparted by the first cable within the shaft in a direction normal to the support beam axis 710 is balanced by an equal and opposite proximal-direction end effector force $F_C'$ resulting in a net force of zero upon the beam due to forces imparted to first cable segments within the shaft. Outside the shaft, however, the offset angled first cable segment 608a exerts a net force $F_C \sin\theta$ normal to the support beam and in response, the support beam produces an opposing reactive force $F_Z$.

A fourth pulley 716 is secured to the chassis 440. A proximal end portion of the second cable 614 wraps about a perimeter groove portion of the fourth pulley 716. A second cable drive mechanism 458b, which is secured to the mechanical ground 708, is configured to impart a second cable force $F_{C2}$ upon the second cable 614 to open the jaws. In some embodiments, the second cable drive mechanism 458b includes a motor driven rotatable spindle mechanically coupled to a proximal end portion of the second cable 614. The fourth pulley 716 and the second cable drive mechanism 458b are disposed level with each other without a vertical offset between them relative to the support beam 702 such no net normal force is exerted by a level second cable segment 614a extending between the fourth pulley 716 and the second cable drive mechanism 458b. The strain force $F_Z$ experienced by the support beam 702 due to the offset angled first cable segment 608a is a reactive force imparted that balances the net first cable force $F_C \sin\theta$ imparted to the support beam 702. The strain force $F_Z$ imparts a strain to the support beam 702 and to the strain sensor 712. The relationship between the net normal force $F_C \sin\theta$ and the strain force $F_Z$ imparted to the strain sensor 702 is represented by the following formulation (2).

$$F_{z,PSC} = F_c \sin\theta + F_{cd} - F_{cp} = F_c \sin\theta = \frac{M_{grip}}{l} \sin\theta \qquad (2)$$

The strain sensor produces a sensor signal $S_S$ that has a magnitude indicative of the magnitude of the strain force $F_{Z,PSC}$, which in turn is proportional to a magnitude of the grip moment $M_{grip}$ about the slave pivot axis, $M_{grip}$. In some embodiments, the signal may be a change in voltage on a Wheatstone bridge (not shown) produced by a resistance change on a strain gauge.

Figure 8:
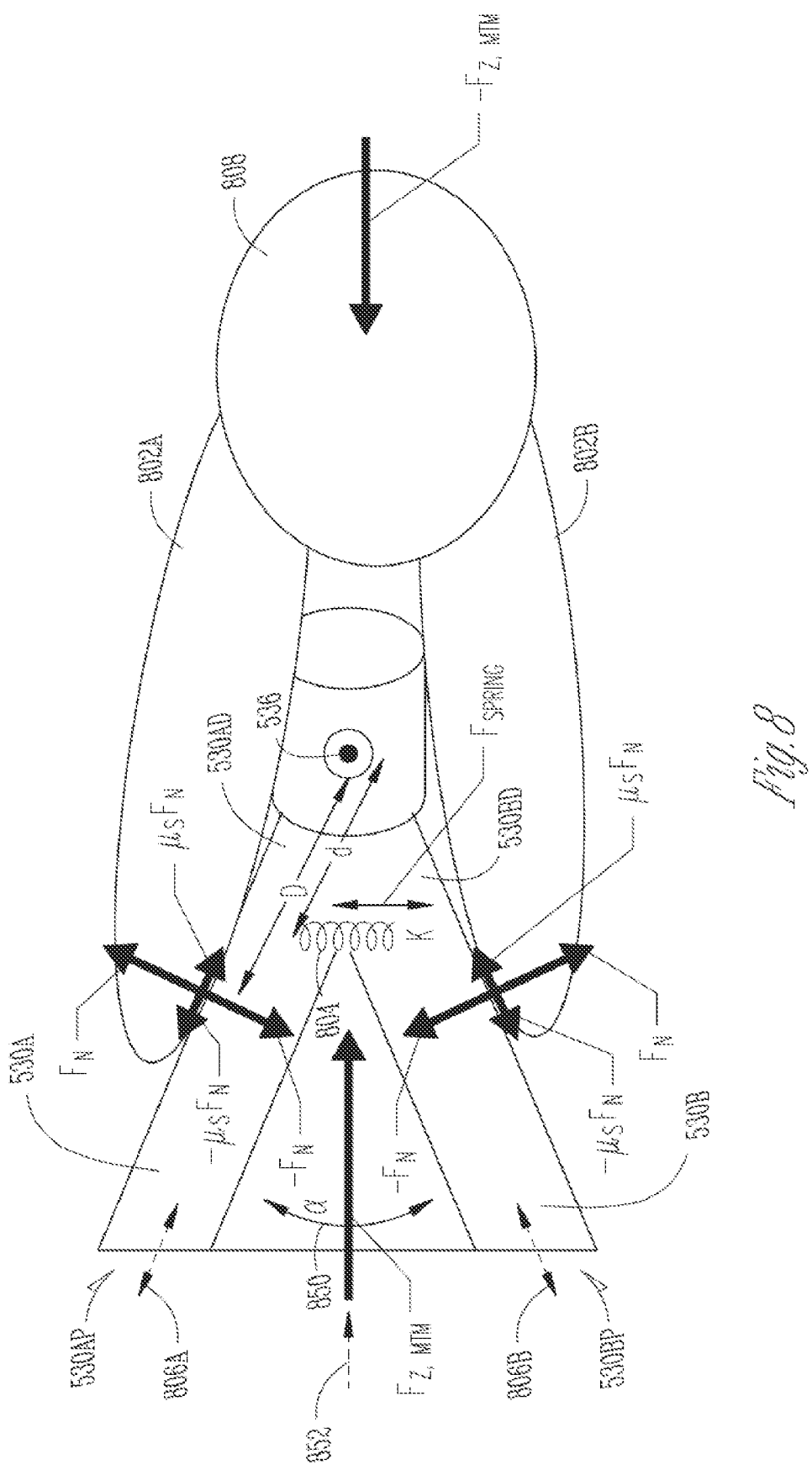
FIG. 8 is an illustrative free body diagram to show forces upon grip members of the master control input of FIG. 5 and a surgeon's fingers in accordance with some embodiments.

FIG. 8 is an illustrative free body diagram to show forces upon the grip members of a master control input and a surgeon's fingers in accordance with some embodiments. During a surgical procedure, a surgeon's fingers are placed on outside grip surfaces of the first and second grip members 530a, 530b. The first and second grip members 530a, 530b have proximal ends 530ap, 530bp and distal ends 530ad, 530bd. The distal ends 530ad, 530bd of the first and second grip members are pivotally mounted to pivot about the master pivot axis 536 and are offset from each other by an angle α. A surgeon's fingers 802a, 802b may apply fingertip forces to the first and second grip members 530a, 530b to move them along the first path 850 about the master pivot axis 536, to move them closer together or farther apart so as to command corresponding movements of the first and second cantilever beams 462, 464 of the end effector 454. Specifically, for example, moving the proximal ends 530ap, 530bp of the first and second grip members 530a, 530b in a direction along the first path 850 to bring them closer together, which reduces the angle α between them, causes the first and second cantilever beams 462, 464 to move closer together, closing the end effector jaws. Conversely, for example, moving the proximal ends 530ap, 530bp of the first and second grip members 530a, 530b in an opposite direction along the first path 850 to space them farther apart from each other, which increases the angle α between them, causes the first and second cantilever beams to move farther apart, opening the end effector jaws. U.S. Pat. No. 6,594,552, which is incorporated in its entirety by this reference above explains grip member control of end effectors in accordance with some embodiments. Thus, the angle α between the distal ends 530ad, 530bd of the first and second grip members determines the positions of the corresponding first and second cantilever beams at the end effector.

More particularly, a bias member, such as a bias spring 804, provides a bias force $F_{spring}$ to urge the first and second grip members 530a, 530b away from each other. A surgeon may apply forces $-F_N$, which are normal to longitudinal axes 806a, 806b of the first and second grip members 530a, 530b. The surgeon-applied force $-F_N$ rotates the first and second grip members along the first path 850 about the master pivot axis 533 to bring their proximal end portions 530ap, 530bp closer together, reducing the angle α, between them, and commanding the imparting of the first cable force $F_C$ to cause the first and second cantilever beams 462, 464 at the end effector 454 to move closer together. Additionally, the surgeon's fingers 802a, 802b may impart surface forces $\mu_s F_N$, which are parallel to surfaces of the first and second grip members 530a, 530b, in combination with the surgeon-imparted normal forces $-F_N$.

The first and second grip members 530a, 530b impart opposite direction normal forces $F_N$ to the surgeon's fingers 802a, 802b in reaction to the surgeon-imparted normal forces $-F_N$. The first and second grip members 530a, 530b also impart opposite direction surface forces $\mu_s F_N$ in reaction to the surgeon-imparted surface forces $\mu_s F_N$.

Thus, in accordance with some embodiments, the first and second cantilever beams 462, 464 correspond to the first and second grip master members 530a, 530b. Larger scale motions imparted by a surgeon's fingers to the master members 530a, 530b are translated to corresponding smaller scale motions of the first and second cantilever beams 462, 464. In particular, in accordance with some embodiments, for example, a rotation of the master members 530a, 530b about the master pivot axis 536 is translated to corresponding rotation of the first and second cantilever beams 462, 464 about slave pivot axis 602. In some embodiments, for example, translation of movement of the master members 530a, 530b translates to corresponding movement of the first and second cantilever beams 462, 464 such that an angle α about the master pivot axis 536 between the master members 530a, 530b matches an angle α slave pivot axis 602 between the first and second cantilever beams 462, 464. It is noted that during routine operation, the surgeon imparted forces and the grip member reaction forces are balanced. During routine operation, a friction force at the grip members 530a, 530b is static friction, which is just enough to match the parallel surface forces applied by the surgeon's fingers 802a, 802b at the grip members. It will be appreciated that reaction surface forces $\mu_s F_N$ are less than a maximum permitted surface friction force $F_{fr}$ at which the grip members 530a, 530b start sliding in the surgeon's fingers 802a, 802b, causing the surgeon's finger's to lose their grip, at which point the surgeon may need to apply an increased normal force to increase the surface friction to stop the sliding. The relationship between surface force $\mu_s F_N$ and maximum permitted $F_{fr}$ is represented by the following formulation.

$$F_{fr,max} = \mu_s F_N \qquad (3)$$

In operation, a moment imparted by a surgeon 18 at distance a D from the master pivot axis 536 equals and is balanced by a moment imparted by the bias spring 804 at a distance d from the pivot axis 536. If it is assumed that a torsional spring has a spring force in indicated in the formulation.

$$F_{spring} = k(\alpha_0 - \alpha) \qquad (4)$$

where k is the spring constant.

If it is assumed that $\alpha_0$ is the initial angular position, then the normal force $F_N$ is directly related to the angle α by the moment balance the following formulation.

$$F_N D = F_{spring} d = k(\alpha_0 - \alpha) d \qquad (5)$$

Thus, $$F_N = \frac{k(\alpha_0 - \alpha)d}{D} \qquad (6)$$

In view of equation (6), it will be appreciated that normal force F N cannot be modulated directly to display the grip force to the surgeon without changing the a, which would be detrimental to performance since it would affect the gripping angle of the first and second cantilever beams 462, 464 at the end effector 454. However, the inventor herein realized that a feedback surface force $F_{z,MTM}$ imparted to mount member 530, and through it, to the first and second grip members 530a, 530b mounted thereon, along a second path 852 in a direction toward the pivot axis 533 and toward a palm 808 of the surgeon's hand may be modulated to increase a surface feedback force imparted to the fingers 802a, 802b to thereby display an indication of a magnitude of the grip force moment $M_{grip}$ at the end effector 454.

An upper limit of the feedback force $F_{z,MTM}$ is dependent on the amount of force required to make the grip members slip against the surgeon's fingers by overcoming static friction:

$$F_{z,MTM} \leq 2 \cdot (F_N \sin\alpha + F_{fr,max} \cos\alpha) = 2 \cdot (F_N \sin\alpha + \mu_s F_N \cos\alpha) \qquad (7)$$

$$F_{z,MTM} \leq 2 \cdot \left(\frac{k(\alpha_0 - \alpha)d}{D}\right) \cdot (\sin\alpha + \mu_s \cos\alpha) \qquad (8)$$

Since all of the values on the right are known (with the exception of the static friction coefficient, which may be estimated), this provides an upper limit for the $F_{z,MTM}$ that can be commanded. A master-side feedback force $F_{Z,MTM}$ may be imparted along the second path 852 toward the grip members 530a, 530b in a direction perpendicular to the master pivot axis 536 to indicate a magnitude of a sensor signal $S_S$, which is indicative of the grip moment $M_{grip}$ at the slave end effector 454. Providing the master-side feedback force along the second path 852 separate from the first path 850 ensures that the user is provided an indication of magnitude of the slave force distinguishable from a bias force provided by the spring 804. Moreover, providing the master-side feedback force in a direction that is perpendicular to the master pivot axis 536 ensures that equal feedback forces are imparted to them, since in accordance with some embodiments, the grip paddles 530a are constrained to be symmetric. More particularly, motors that control the gimbal assembly 528 may be controlled to impart a feedback force $F_{Z,MTM}$ to the handle 530 upon which the first and second grip members 530a, 530b are mounted that may be sensed by a surgeon through fingers 802a, 802b and that provide an indication of slave grip force $F_{grip}$. Moreover, a magnitude of the feedback force $F_{Z,MTM}$ may be modulated according to a magnitude of the sensor signal $S_S$, which is indicative of a magnitude of the grip moment $M_{grip}$ and the slave grip force $F_{grip}$.

In some embodiments, a magnitude of a surface feedback force transferred to the fingers 802a, 802b is the friction component of the force:

$$F_{z,MTM} = 2 \cdot (F_N \sin\alpha + F_{fr} \cos\alpha) \quad (9)$$

$$F_{fr} = \frac{F_{z,MTM}}{2 \cdot \cos\alpha} - \frac{k(\alpha - \alpha_0)d \cdot \tan\alpha}{D} \quad (10)$$

For a given angle $\alpha$ this friction force $F_{fr}$ felt at the fingers 802a, 802b is linear with the feedback surface force $F_{Z,MTM}$ and therefore, the feedback force $F_{Z,MTM}$ can be modulated linearly to control the surface feedback friction component $F_{fr}$ of the feedback force $F_{Z,MTM}$ that is felt by the surgeon and to limit the feedback friction component $F_{fr}$ to a magnitude less than an magnitude required to make the grip members 530a, 530b slip against the surgeon's fingers. Maintaining a feedback force within the upper limit ensures that finger slippage does not occur that may cause pivotal movement pivotal of the grip members 530a, 530b about the master pivot axis 536 that could be translated to movement of the cantilever beams 462, 464 about the slave pivot axis 602. In other words, the shear force upper limit ensures that a feedback force intended to a feedback force to display to a surgeon a magnitude of a slave grip force at the end effector 454 does not cause a change in rotational positions of the cantilever beams 462, 464 at the end effector 454.

Figure 9:
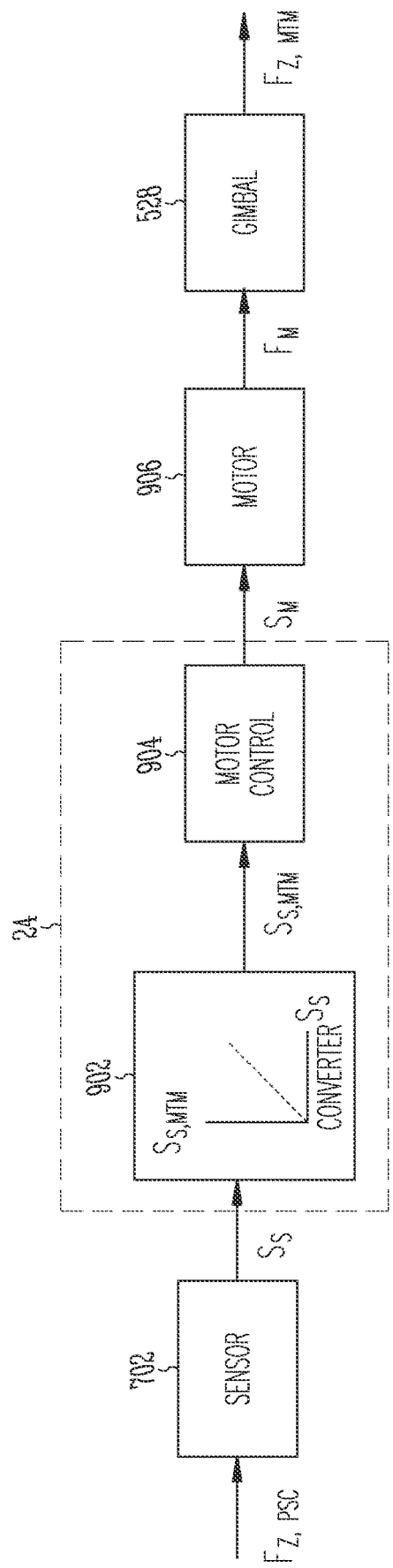
FIG. 9 is an illustrative control system flow diagram representing a transformation of a reactive beam force to a feedback force in accordance with some embodiments.

FIG. 9 is an illustrative control system flow diagram 900 representing a transformation of a reactive beam force to a feedback force in accordance with some embodiments. A reactive beam force $F_{Z,PSC}$ imparts a strain go the sensor 712, which produces a sensor signal $S_S$ having a magnitude that is proportional to a magnitude of the reactive beam force $F_{Z,PSC}$, which is proportional to a grip moment $M_{grip}$ and a slave grip force $F_{grip}$. A converter block 902 converts the sensor signal $S_S$ to a feedback force master control signal $S_{S,MTM}$. In some embodiments, the converter block 902 produces an $S_{S,MTM}$ signal having a magnitude that is a linear function of a magnitude of the sensor signal $S_S$. A motor control block 904 is configured to produce one or more motor control signals $S_M$ in response to the $S_{S,MTM}$ signal, to control motors 906 that produce forces F M to control motion of the gimbal assembly 528 to impart a feedback force $F_{Z,MTM}$ having a magnitude that is proportional to a magnitude of the $S_{S,MTM}$ signal and that is limited to avoid slippage of the first and second master grip members 530a, 530b in a surgeon's fingers. In some embodiments, the computer processors located on the electronics cart 24 are configured to determine the $S_{S,MTM}$ signal as a linear function of the $S_S$ signal. Moreover, in some embodiments, the computer processors located on the electronics cart 24 are configured to produce the one or more motor control signals S M based upon the $S_{S,MTM}$ signal. In various other embodiments, the motor control signals S M can cause an oscillating (e.g., vibrating) feedback force $F_{MTM}$ (not shown) at the master having a second path that is an oscillation path separate from the first path and having a parameter proportional to a magnitude of the $S_{S,MTM}$ signal (e.g., amplitude or frequency of oscillation of force $F_{MTM}$).

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. For example, although mechanically supported masters are depicted and described for exemplary purposes, in various embodiments the masters can be wireless or connected to the system only by wires ("ungrounded"). In one alternative embodiment, for example, a master may include a joy stick grip member mounted to a mount member, wirelessly coupled to control a slave end effector in response to movement of the joy stick. In another alternative embodiment, for example, a master may include a pistol trigger grip member in which a trigger grip member is mounted to a pistol-shaped mount member, wirelessly coupled to control a slave end effector in response to movement of the trigger. Thus, the scope of the disclosure should be limited only by the following claims, and it is appropriate that the claims be construed broadly and in a manner consistent with the scope of the embodiments disclosed herein. The above description is presented to enable any person skilled in the art to create and use a surgical system having an end effector force coupled to provide a corresponding master controller feedback force. Various modifications to the embodiments will be readily apparent to those skilled in the art, and the generic principles defined herein may be applied to other embodiments and applications without departing from the scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

The invention claimed is:

1. A teleoperated surgical system comprising:
   a surgical instrument including an end effector, the end effector having an end effector pivot axis;
   a master tool manipulator operably coupled to the end effector, the master tool manipulator including a grip member movable along a first path; and
   a control system operably coupled to the surgical instrument and the master tool manipulator, the control system including at least one processor;
   wherein the control system performs a plurality of operations including:
      moving the end effector about the end effector pivot axis in response to a movement of the grip member along the first path,
      determining a magnitude of a moment about the end effector pivot axis resulting from the moving of the end effector, and
      providing a feedback force to the master tool manipulator along a second path, the second path being different from the first path, and the feedback force being based at least in part on the magnitude of the moment about the end effector pivot axis.

2. The teleoperated surgical system of claim 1, wherein:
the teleoperated surgical system includes a sensor operably coupled to the surgical instrument; and
the sensor is positioned to output a sensor signal having a magnitude indicative of the moment about the end effector pivot axis.

3. The teleoperated surgical system of claim 2, wherein:
the sensor signal is associated with a strain; and
determining the magnitude of the moment includes determining the magnitude of the moment based on a magnitude of the strain.

4. The teleoperated surgical system of claim 1, wherein:
the second path is in a direction toward a palm of a hand of an operator on a condition that the hand of the operator is engaged with the master tool manipulator.

5. The teleoperated surgical system of claim 4, wherein:
the plurality of operations includes establishing the feedback force at a magnitude less than a magnitude required to cause the grip member to slip within the hand of the operator.

6. The teleoperated surgical system of claim 1, wherein:
the master tool manipulator has a master tool manipulator pivot axis; and
the grip member is pivotably coupled to move about the master tool manipulator pivot axis along the first path.

7. The teleoperated surgical system of claim 6, wherein:
the second path is perpendicular to the master tool manipulator pivot axis.

8. The teleoperated surgical system of claim 6, wherein:
the master tool manipulator includes a handle;
the grip member includes an end pivotably coupled to the handle at the master tool manipulator pivot axis;
the handle defines a first longitudinal axis orthogonal to the master tool manipulator pivot axis; and
the second path is parallel to the first longitudinal axis.

9. The teleoperated surgical system of claim 8, wherein:
the grip member defines a second longitudinal axis that extends perpendicular to the master tool manipulator pivot axis;
the second longitudinal axis intersects the first longitudinal axis; and
the movement of the grip member along the first path changes an angle defined by the intersection of the first longitudinal axis and the second longitudinal axis.

10. The teleoperated surgical system of claim 6, wherein:
the grip member is a first grip member;
the master tool manipulator includes a second grip member;
the first grip member and the second grip member are coupled to pivot with reference to one another about the master tool manipulator pivot axis; and
the second grip member is movable along the first path.

11. The teleoperated surgical system of claim 10, wherein:
the feedback force is based at least in part on a magnitude of a moment about the master tool manipulator pivot axis and an angular separation between the first grip member and the second grip member relative to the master tool manipulator pivot axis.

12. The teleoperated surgical system of claim 11, wherein:
the feedback force is delivered along the second path without altering the angular separation between the first grip member and the second grip member relative to the master tool manipulator pivot axis.

13. The teleoperated surgical system of claim 10, wherein:
the master tool manipulator further includes a bias member positioned to urge the first grip member apart from the second grip member along the first path.

14. The teleoperated surgical system of claim 13, wherein:
the bias member includes a spring that has a spring constant; and
the feedback force is based at least in part on the magnitude of the moment about the master tool manipulator pivot axis, an angular separation between the first grip member and the second grip member relative to the master tool manipulator pivot axis, and the spring constant.

15. The teleoperated surgical system of claim 10, wherein:
the end effector includes a first jaw and a second jaw pivotally coupled to pivot with reference to one another about the end effector pivot axis;
the first jaw is pivotable about the end effector pivot axis in response to a movement of the first grip member along the first path; and
the second jaw is pivotable about the end effector pivot axis in response to a movement of the second grip member along the first path.

16. The teleoperated surgical system of claim 15, wherein:
the surgical instrument includes an elongated hollow shaft, a plurality of tension members extending within the elongated hollow shaft and operably coupled to the first jaw and the second jaw, and one or more actuators operably coupled to the plurality of tension members;
the shaft includes a distal end portion and a proximal end portion; and
the first jaw and the second jaw are pivotally coupled to pivot with reference to one another about the end effector pivot axis at the distal end portion of the shaft.

17. The teleoperated surgical system of claim 16, wherein:
the plurality of tension members includes one or more tension members coupled to cause the first jaw to rotate about the end effector pivot axis in response to a force imparted to the one or more tension members.

18. The teleoperated surgical system of claim 17, wherein:
the one or more actuators are arranged to impart the force to the one or more tension members to cause the first jaw to rotate toward the second jaw in response to a movement of the first grip member relative to the master tool manipulator pivot axis.

19. The teleoperated surgical system of claim 17, wherein:
the one or more actuators are arranged to impart the force to the one or more tension members to cause the first jaw and the second jaw to pivot about the end effector pivot axis in response to a movement of the first grip member and the second grip member relative to the master tool manipulator pivot axis; and
the pivoting of the first jaw and the second jaw about the end effector pivot axis reduces an angular separation between the first jaw and the second jaw.

20. The teleoperated surgical system of claim 19, wherein:
the angular separation between the first jaw and the second jaw is a gripping angle of the end effector; and
the feedback force is delivered along the second path without altering the gripping angle of the end effector.

* * * * *